United States Patent [19]
Kolbel et al.

[11] 3,937,685
[45] Feb. 10, 1976

[54] POLYGLYCIDYL ETHERS

[75] Inventors: Herbert Kölbel; Georg Manecke; Eftichia Güttler-Pimenidou, all of Berlin, Germany

[73] Assignee: Hoechst Aktiengesellschaft, Germany

[22] Filed: Nov. 19, 1973

[21] Appl. No.: 417,120

[30] Foreign Application Priority Data
Nov. 21, 1972 Germany............................ 2256947

[52] U.S. Cl..... 260/47 EP; 260/47 EA; 260/47 EN; 260/348 R
[51] Int. Cl.²......................................... C08G 30/04
[58] Field of Search........ 260/47 EP, 348 R, 348 A, 260/348.6, 590, 64

[56] References Cited
UNITED STATES PATENTS

| | | | |
|---|---|---|---|
| 2,694,694 | 11/1954 | Greenlee | 260/47 |
| 3,410,824 | 11/1968 | Atkinson | 260/47 |
| 3,553,165 | 1/1971 | Kiryu | 260/47 |

*Primary Examiner*—Donald E. Czaja
*Assistant Examiner*—T. Pertilla
*Attorney, Agent, or Firm*—Gordon W. Hueschen

[57] ABSTRACT

The object of the invention are new polyglycidyl ethers and a method for their production, which ethers give a new mixture of the type mentioned which can be cured like a thermosetting resin, that is to say an epoxide resin system which can be cross-linked to give thermosetting resin compositions, which possess improved heat distortion points and good mechanical properties, and especially no excessive brittleness.

14 Claims, No Drawings

NEW POLYGLYCIDYL ETHERS

BACKGROUND OF THE INVENTION

The invention relates to new polyglycidyl ethers and their manufacture and use for epoxide resin systems.

Mixtures which contain polyglycidyl ethers of diphenols and curing agents, and which can be cured like thermosetting resins, are known and are also described as epoxide resin systems. The heat resistance, mechanical properties and chemical resistance of the thermosetting resins obtainable from such systems by thermally and/or catalytically initiated crosslinking have to meet high and indeed rising standards. The problem of combining maximum heat distortion point, say measured with the aid of the socalled Martens temperature, with good mechanical properties has, however, not been solved completely satisfactorily in the case of such thermosetting resins, in spite of intensive research effort.

Thus, for example, the best heat distortion points achieved with the previously known optimum epoxide resin systems, such as cycloaliphatic epoxide resin/hexahydrophthalic anhydride, bisphenol-epoxide resin/pyromellitic anhydride, novolac-epoxide resin/diaminodiphenylsulphone or novalac-epoxide resin/diaminodiphenylmethane, are of the order of magnitude of 150° – 185°C. For many fields of use of such thermosetting resins, heat distortion points of 200°C and above would be very desirable but in previous experiments aimed in this direction such heat distortion points were only achievable, if at all, at the expense of other important properties, especially impact strength, or flexural strength as a measure of brittleness.

SUMMARY

The object of the invention are new polyglycidyl ethers and a method for their production, which ethers give a new mixture of the type mentioned which can be cured like a thermosetting resin, that is to say an epoxide resin system which can be crosslinked to give thermosetting resin compositions, which possess improved heat distortion points and good mechanical properties, and especially no excessive brittleness.

In order to achieve this aim, the possibility of utilising dihydroxychalcones, that is to say compounds of the general formula

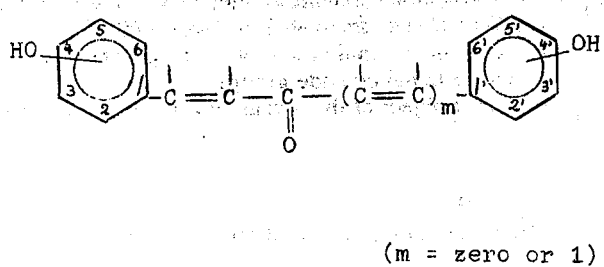

(m = zero or 1)

as diphenols for forming polyglycidyl ether for epoxide resin systems was first investigated though known dihydroxychalcones, whilst having proved suitable for the manufacture of polycarbonates, have — in the form of the polyglycidyl ethers — only been regarded as suitable for such special cases of the application of epoxides wherein the heat distortion point of the cured composition is of no practical importance.

The results of this investigation appeared first to confirm the inadequate suitability of the known dihydroxychalcones as polyglycidyl ethers for epoxide resin systems in that these polyglycidyl ethers, when used with most of the customary epoxide resin curing agents which were tested, did not offer a satisfactory solution of the problem of the heat distortion point. With one exception, any achievable increases in the heat distortion point were in fact only achievable at the expense of embrittlement of the cured composition.

Surprisingly, however, it was then found that the polyglycidyl ethers of certain dihydroxychalcones permit a substantial increase in the heat distortion point of the thermosetting resin compositions manufactured from them, whilst these compositions still show good mechanical properties, especially with regard to impact strength and flexural strength, and excellent solvent resistance.

These dihydroxychalcones correspond to the formula (II)

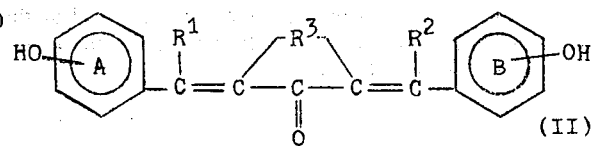

(II)

in which $R^1$ and $R^2$ are identical or different and are hydrogen atoms or methyl, ethyl, propyl, iso-propyl groups, and $R^3$ is a straight-chain or branched alkylene group with 2 to 4 C atoms, preferably 3 C atoms, in the main chain and a methyl, ethyl, n-propyl, iso-propyl or iso-butyl group in the branch chain, it being possible for the nuclei A and B each to possess one or more identical or different non-epoxidisable substituents, such as methyl, ethyl, n-propyl, iso-propyl, methoxy, ethoxy, n-propoxy or iso-propoxy groups.

As a general rule, it was found that dihydroxychalcones of the formula (II), in the form of their polyglycidyl ethers (I) can be crosslinked with customary epoxide resin curing agents in accordance with the methods customary in epoxide resin application technology, to give thermosetting compositions of substantial heat distortion points, which possess good mechanical properties, especially elasticity and excellent solvent resistance.

Preferred compounds of the formula (II) are, inter alia, compounds in which $R^1$ and $R^2$ represent hydrogen atoms, $R^3$ is the propylene or i-butylene group and the nuclei A and B, apart from the hydroxyl groups preferably present in the 4- or 4'-position, are either unsubstituted or monosubstituted by epoxidisable substituents which preferably produce little or no polarising effect, such as the methoxy group.

Special examples of dihydroxychalcones of the formula (II) are bis-2,6-(p-hydroxybenzal)-cyclohexanone-(1), bis-2,6-(p-hydroxybenzal)-4-methyl-cyclohexanone-(1), bis-2,6-(3-methoxy-4-hydroxy-benzal)-cyclohexanone-(1) and bis-2,6-(3-methoxy-4-hydroxy-benzal)-4-methyl-cyclohexanone-(1). Bis-2,5-(p-hydroxybenzal)-cyclopentanone-(1) is a further, though less preferred, example, since here the group $R^3$ only suffices to form a cyclopentanone ring but not to form a cyclohexanone ring, optionally substituted by alkyl groups which leads to the formation of an aplanar dihydroxychalcone structure. Such an aplanar configuration, as results in the base of the optionally alkyl-substituted cyclohexanone ring as a result of the methylene group in the para-position to the carbonyl-C atom, is preferred because it gives lower melting points of the polyglycidyl ethers manufactured from such dihydroxychalcones.

The compounds of the formula (II) are preferably manufactured by condensation of about 2 mols of the corresponding hydroxybenzaldehyde of the formula (2a

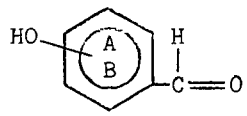

(2a)

which can, as indicated for the aromatic nuclei A and B in the case of the formula (II), possess one or more nonepoxidisable substituents, with about 1 mol of the corresponding α,α-di-unsubstituted cycloaliphatic ketones of the formula (2b)

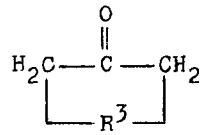

(2b)

in which $R^3$ has the abovementioned meaning. Examples of aldehydes of the formula (2a) are p-hydroxybenzaldehyde and vanillin. Examples of ketones of the formula (2b) are cyclopentanone, cyclohexanone and methylcyclohexanone-(4).

The condensation of aldehydes and ketones of the type mentioned can be carried out under alkaline or acid conditions, but the acid-catalysed condensation is preferred. Adducts formed as intermediates can be hydrolysed without difficulties.

The dihydroxychalcones of the formula (II), thus obtainable, can be used in a purified or crude form for the manufacture of new polyglycidyl ethers (I) which schematically correspond to the formula in which $R^4$ denotes hydrogen atoms or methyl groups, $n$ denotes zero or an integer from 1 to about 20 and M denotes a chalcone radical of the formula

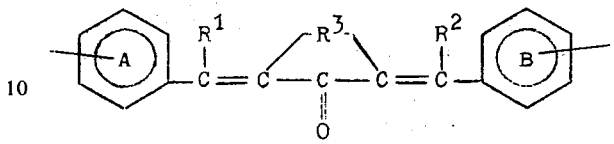

(Ia)

in which the symbols have the meanings indicated in conjunction with the formula (II), which are the object of the present invention.

Since $n$ in the formula (I) can be zero, the diglycidyl ethers are also included amongst the new polyglycidyl ethers of the formula (I).

The manufacture of the polyglycidyl ethers (I) frequently yields mixtures with different values of $n$, for which reason the epoxide value (determined in pyridine according to Greenlee, see, for example, U.S. Pat. No. 2,852,447) of the ether or the ether mixture or the ratio of effective epoxide value to theoretical epoxide value can also be employed for the additional characterisation of suitable and preferred polyglycidyl ethers (I).

In preferred polyglycidyl ethers (I), the epoxide value (in milliequivalent/g) is at least 1.9. Furthermore, the ratio of the actual epoxide value to the theoretical epoxide value of the preferred ethers is at least 0.4.

The new polyglycidyl ethers of the formula (I) can be manufactured from the corresponding dihydroxychalcones of the formula (II) in various ways common in the field of epoxy resins, say by addition of epichlorohydrins of the formula

(III)

in which $R^4$ has the mentioned meaning, to the phenolic OH-groups of the hydroxychalcones of the formula (II) to form the bis-chlorohydrin ethers or higher ethers and subsequent elimination of hydrogenchlorine to form the terminal epoxide groups.

A further object of the invention is a method for the

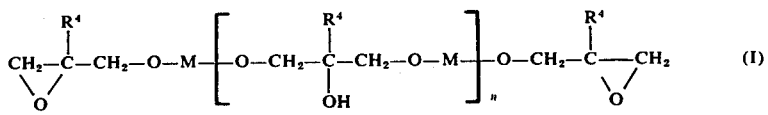

(I)

production of polyglycidyl ethers of the formula

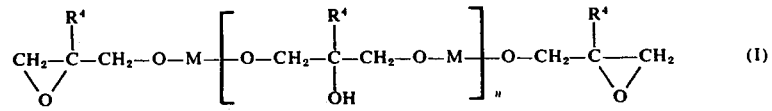

(I)

in which R⁴ denotes hydrogen atoms or methyl groups, n denotes zero or an integer from 1 to about 20 and M denotes a chalcone radical of the formula

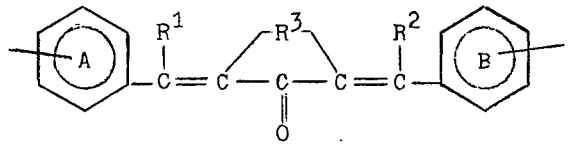

(Ia)

in which the substitutents R¹ and R² are identical or different and denote hydrogen atoms or methyl, ethyl, n-propyl, iso-propyl groups and R³ denotes a straight chained or branched chain alkylene group of 2 to 4 carbon atoms, preferably of 3 carbon atoms in the main chain, and a methyl, ethyl, n-propyl, iso-propyl or iso-butyl group as the branch, it being possible for the nuclei A and B each to possess one or more equal or different nonepoxidisable substituents, such as methyl, ethyl, n-propyl, iso-propyl, methoxy, ethoxy, n-propoxy or iso-propoxy groups, characterised in that dihydroxychalcones of formula

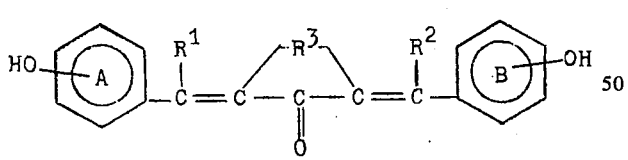

(II)

are reacted with epichlorohydrines of formula

(III), in the presence of alkali, with the molar ratio of dihydroxychalcone (II) to epichlorohydrine (III) of 1 : 1.25 to 1 : 30, at a temperatur of 25°–110°C, preferably 30° – 95°C.

A special embodiment (a) of the method for the production of glycidyl ethers of the formula

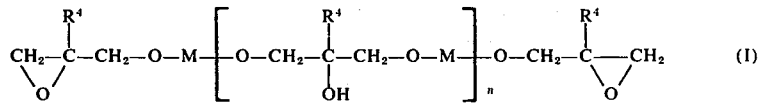

(I)

in which the main portion of polyglycidyl ether (I) is obtained with n denoting zero, is characterised in that dihydroxychalcones of the formula

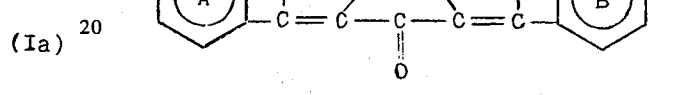

(II)

are reacted with 3 to 15 mols epichlorohydrin (III) per mol phenolic hydroxyl group in the presence of alkali and at a temperature of 50° to 110°C, preferably 75° –95°C.

Another special embodiment (b) of the method for the production of glycidyl ethers of the formula

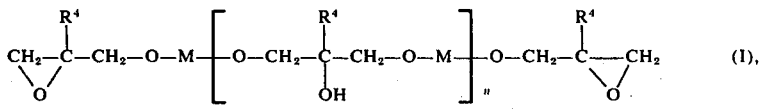

(I), in which n denotes 1 to 20, is characterised in that dihydroxychalcones of the formula

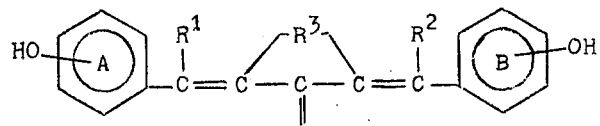

(II)

are reacted with epichlorohydrin (III) in a molar ratio of 1 : 1.25 to 1 : 1.75 in the presence of alkali at temperatures of 30° to 75°C, preferably 30° – 60°C.

A more special embodiment (c) of the method according to embodiment (a) is characterised in that the reaction is carried out in the presence of about one equivalent of solid alkali hydroxide or of a concentrated aqueous alkali hydroxide solution per phenolic hydroxyl group as well as in the presence of 0.05 – 5 percent by weight of choline or choline salts or mixtures thereof as catalyst, at raised temperature and subsequent separation of excess epichlorohydrin together with water from the reaction mix by distillation and isolation of the formed glycidyl ether whereby the alkali is added over the course of 30 to 300 minutes to the reaction mix in which 2 to 8 percent water are present and also the water formed during the reaction, and whereby the heat of reaction and optionally the water added together with the alkali are removed by distillation.

According to a further preferred process, the dihydroxychalcone (II) is reacted with epichlorhydrin (III) in the molar ratio of 1 : 5, using reaction times of about 1 hour and temperatures of about 90°C, sodium hydroxide being added in excess or in approximately stoichiometric amount. Preferably, the stoichiometric amount of sodium hydroxide is first added and in the last one-third of the reaction additional sodium hydroxide is added to complete the elimination of hydrogen chlorine. The epoxide values of the products can be increased by working under anhydrous conditions (methanolic potassium hydroxide), though in most cases the yield is reduced.

The polyglycidyl ethers (I) can be obtained as resins of various viscosities and can be used either as such or in the purified form for epoxide resin systems. It is also possible to use mixtures of polyglycidyl ethers (I) with different meanings of M, in accordance with the possible variations of this group as explained in the context of the formula (II).

Suitable curing agents for the new polyglycidyl ethers of the formula (I) are the known epoxide curing agents, most cases. Mixtures of different curing agents can also be used.

The polyglycidyl ethers (I) of the dihydroxychalcones (II) can generally be used in the manner customary for epoxide resins.

In the examples which follow, for the manufacture of the dihydroxychalcones (II), of the corresponding polyglycidyl ethers (I) and of epoxide resin systems prepared therefrom, the data in per cent are by weight.

Manufacture of the dihydroxychalcones (Formula II)

Dry hydrogen chlorine gas is passed into a saturated solution of about 2 mols of aldehyde and about 1 mol of ketone in absolute methanol (approx. 50 to 150 ml) in a 250 ml two-neck flask having a gas inlet and gas outlet and magnetic stirrer, the mixture being cooled with ice. The solution immediately assumes a deep colouration. After some time crystallisation commences and can go as far as solidification of the reaction mixture. The resulting paste of crystallites and solvent is filtered with suction, whilst being pressed out. The solid, which is the hydrochloride of the chalcone of the formlula (II), is subsequently decomposed in water and can optionally be reprecipitated from acetone/water, methanol/water or dioxane/water. The products are yellow to green in colour and are obtained in yields of up to 98%.

In this way, the starting compounds indicated in Table I below were converted to the dihydroxychalcones (II) which are also indicated in the Table.

TABLE I

| Example preliminary product | Starting compound Aldehyde | Ketone | Dihydroxychalcone | melting point (°C) | Yield (%) |
| --- | --- | --- | --- | --- | --- |
| 1 | p-Hydroxybenzaldehyde | Cyclohexanone | Bis-2,6-(p-hydroxybenzal)-cyclohexanone-(1) | 295 | 94 |
| 2 | p-Hydroxybenzaldehyde | Methylcyclohexanone-(4) | Bis-2,6-(p-hydroxybenzal)-4-methyl-cyclohexanone-(4) | 214 | 65 |
| 3 | Vanillin | Cyclohexanone | Bis-2,6-(3-methoxy-4-hydroxybenzal)-cyclohexanone-(1) | 183 | 98 |
| 4 | Vanillin | Methylcyclohexanone-(4) | Bis-2,6-(3-methoxy-4-hydroxybenzal)-4-methyl-cyclohexanone-(1) | 161 | 48 |
| 5 | p-Hydroxybenzyldehyde | Cyclopentanone | Bis-2,5-(p-hydroxybenzal)-cyclopentenone-(1) | 350 decomp. | 72 | especially the anhydrides of organic acids and aromatic amines, but also aliphatic and cycloaliphatic polyamines. Special examples of suitable curing agents are, inter alia, succinic anhydride, isooctylsuccinic anhydride, maleic anhydride and its methyl homologues, phthalic anhydride, tetrahydrophthalic anhydride, methylnadic anhydride, 4,4'-diaminodiphenylmethane and 4,4'-diaminodiphenylsulphone. These and further curing agents are in themselves known. The proportion of curing agent used in each case is not particularly critical and can be varied within limits, for example 50 to 225% of the stoichiometrically required amount. The optimum proportion of curing agent for a particular purpose depends on the customary parameters, such as curing time, curing temperature, the possible use of initiators and the intended mechanical properties of the cured composition and can be determined in the usual way. In order to obtain Martens temperature values (heat distortion points) above 200°C, amounts of curing agent of between about 50 and about 150% of the stoichiometrically required amount are suitable in Instead of the acid-catalysed condensation described above, it is also possible to employ condensation under alkaline conditions, for example in ethanolic solution of the reactants, with addition of concentrated alkali and prolonged reaction at 35° – 45°C. However, in most cases this gives lower yields.

EXAMPLES 1 to 5

Manufacture of the polyglycidyl ethers (Formula I)

0.1 mol of dihydroxychalcone and 0.2 mol of sodium hydroxide are dissolved in 50 ml of water in a 250 ml flask with reflux condenser and magnetic stirrer. 0.5 mol of epichlorohydrin is added to the homogeneous solution. The reaction mixture is warmed to 90°C. The course of the reaction can be followed through the mixture becoming lighter. After approx. 40 minutes, a further 0.1 mol of sodium hydroxide in 10 ml of water is added. After a total of 1 hour, the reaction is stopped. The aqueous phase is decanted and the resin — if necessary after prior cooling to −30°C — is finely ground in a mortar and washed until it is free of alkali.

The suction-filtered product is dried in a good vacuum at room temperature.

In this way, the polyglycidyl ethers (I) indicated in Table II below are obtained from the dihydroxychalcones (II).

Table II

| Example | Yield (%) | Polyglycidyl ether (Formula (I)) | | | |
|---|---|---|---|---|---|
| | | Colour | Epoxide Valve E (milli-equivalent/g) | E/E$_{max}$ | Melting range (°C) |
| 1 | 96 | Yellow | 2.96 | 0.62 | 70–180 |
| 2 | 97 | Orange | 3.47 | 0.75 | 60–90 |
| 3 | 95 | Yellow-green | 1.95 | 0.44 | 100–160 |
| 4 | 98 | Orange | 2.27 | 0.56 | 65–70 |
| 5 | 94 | Yellow | 1.97 | 0.40 | 300 |

Preparation of the mixture with curing agents, and manufacture of mouldings

The polyglycidyl ethers (I) of Example 1–4 are fused gently, that is to say without local overheating, whilst stirring, a predetermined amount of curing agent is added at 150° – 170°C and the mixture is homogenised. It is then poured into appropriately preheated moulds. The steel moulds, which can be dismantled, are first treated with silicone grease as a release agent. To manufacture mouldings, this mixture can be poured directly into preheated moulds provided with release agent (silicone grease).

The following compounds, in proportions of 25 to 225 %, especially 100 – 150 %, of the stoichiometric amounts, are used as curing agents:
Maleic anhydride (MA)
Succinic anhydride (SA)
Phthalic anhydride (PA)
Isooctenylsuccinic anhydride (IOSA)
Methylnadic anhydride (MNA)
4,4'-Diaminodiphenylsulphone (DDS)
4,4'-Diaminodiphenylmethane (DDM)

The heat distortion points determined according to DIN 53,458 (Martens temperature in °C) of mouldings of the polyglycidyl ethers of Examples 1–4, in each case with 100% of the stoichiometric amount of maleic anhydride, are indicated in Table III below, together with the duration and temperature of the principal curing reaction. All mouldings are precured for 2 hours at 100°C before the principal curing reaction.

Table III

| | t* | Martens temperature (°C) | | | | |
|---|---|---|---|---|---|---|
| Temperature of principal curing reaction (°C) | | 120 | 150 | 180 | 210 | 240 |
| Example 1 | 20 | 129 | 158 | 202 | 257 | 265+ |
| | 40 | 136 | 175 | 215 | 265+ | 265+ |
| | 100 | 139 | 186 | 242 | 265+ | 265+ |
| | 200 | 141 | 194 | 265+ | 265+ | 265+ |
| | 20 | 104 | 1129 | 193 | 228 | 218 |

Table III-continued

| | t* | Martens temperature (°C) | | | | |
|---|---|---|---|---|---|---|
| Temperature of principal curing reaction (°C) | | 120 | 150 | 180 | 210 | 240 |
| Example 2 | 40 | 110 | 137 | 199 | 242 | 231 |
| | 100 | 115 | 144 | 201 | 256 | 230 |
| | 200 | 128 | 145 | 207 | 265 | 214 |
| Example 3 | 20 | 97 | 110 | 150 | 160 | 172 |
| | 40 | 102 | 117 | 183 | 205 | 202 |
| | 100 | 105 | 123 | 207 | 242 | 207 |
| | 200 | 105 | 127 | 213 | 242 | 193 |
| Example 4 | 20 | 95 | 123 | 178 | 192 | |
| | 40 | | | | 204 | |
| | 100 | 104 | 136 | 208 | 220 | |
| | 200 | | | | 220 | | t* = Duration of the principal curing reaction in hours.
The symbol "+" denotes that the upper limit of measurement was exceeded.

The heat distortion points, determined as described above, of mouldings obtained from the polyglycidyl ether according to Example 1 with various curing agents, in each case in proportions of 100 % of the stoichiometric amount, are indicated in Table IV below, together with the temperature of the principal curing reaction (duration 20 hours). All mouldings are precured for 2 hours at 100°C before the principal curing reaction.

Table IV

| Curing agent | Temperature of the principal curing reaction (°C) | | | |
|---|---|---|---|---|
| | 150 | 180 | 210 | 240 |
| SA | 124 | 128 | 135 | 141 |
| PA | 146 | 149 | 156 | 177 |
| MNA | 154 | 215 | 248 | 220 |
| DDS | 165 | 178 | 189 | 179 |

Table V below gives various test data for cross-linked compositions manufactured from polyglycidyl ethers (I) of Example 1 – 4 and maleic anhydride as the curing agent (100 % of the stoichiometric amount). The test specimens were in each case precured for 2 hours at 100°C and fully cured at 210°C for the time indicated in the table.

In addition to the Martens temperatures determined as indicated above, the following are also indicated where appropriate: The Vicat temperatures which are also suitable for assessing the resistance to heat distortion (measured according to VDE 0302/III in °C), the impact strength (determined according to DIN 53,453/DIN 51,222, quoted in cm.kp/cm²), the flexural strength (determined according to DIN 53,452/DIN 51,220/DIN 51,221, indicated in cm.kp/cm²), the modulus of elasticity (determined according to Nitsche, Wolf and Nowak, Practical Testing of Plastics, Berlin 1961), the ball indentation hardness (determined according to DIN 53,456/1963 with maximum instrument deflection of 0.091 mm under maximum test load, quoted in kp/cm²) and data on solvent resistance; these data are also given in comparison with commercially available compositions.

Table V

| | Example | | | | Comparison |
|---|---|---|---|---|---|
| | 1 | 2 | 3 | 4 | |
| Duration of principal curing reaction (hours) | 40 | 200 | 100 | 100 | |
| Martens temperature (°C) | > 265 | 265 | 242 | 220 | 60–125 |
| Vicat temperature (°C) | > 300 | > 300 | > 300 | > 300 | 60–150 |
| Impact strength (cm.kp/cm²) | 6 | 3 | 4 | 3 | 8–20 |
| Flexural strength (cm.kp/cm²) | 920 | 890 | | | 700–1,400 |
| Modulus of elasticity (kp/cm²) | 30,900 | 32,800 | | | approx. 30,000 |
| Ball indentation hardness (10s) (kp/cm²) | 1,300 | 1,520 | 1,375 | 1,395 | 900–1,800 |

The tested crosslinked compositions from the new polyglycidyl ethers (I) described here generally show conspicuously good solvent resistance. For example, no change in weight was found after 30 days' storage of the test specimens in acetone, dioxane, benzene and benzine. The resistance to alkali, acid and water was also very good.

The resistance of the crosslinked compositions to heat aging (storage at 300°C and measurement of the weight decrease in per cent) is outstanding. Whilst compositions of commercially available epoxide systems mostly decompose rapidly at 300°C, compositions of cured polyglycidyl ethers according to the invention only slowly lose weight and a significant shrinkage only occurs after some hours and the weight loss approaches a limiting value after some time, for example after 100 hours at 300°C.

In general, polyglycidyl ethers according to the invention can be used for cured compositions of the most diverse kind, for example for casting compositions and impregnating and insulating material, especially in the electrical industry, as adhesives, for example adhesives for concrete, as acid-resistant putty, as adhesion promoters, for example for safety glass, as a laminating material, for example in aircraft construction and rocket construction, as auxiliaries for paper and textile technology and generally for self-supporting or non-selfsupporting structures, as the principal polymer component or as an additive.

What is claimed is:

1. A polyglycidyl ether of the formula

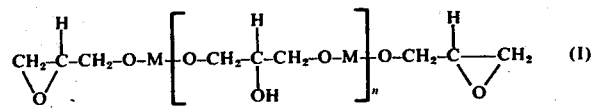

in which
n denotes zero or an integer of 1 to about 20, and
M denotes a chalcone radical of the formula

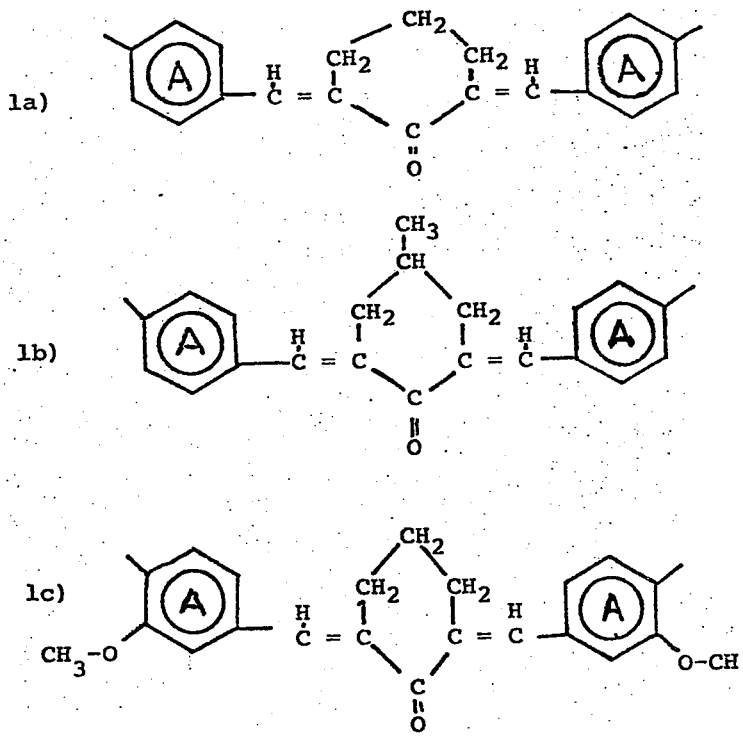

1d) 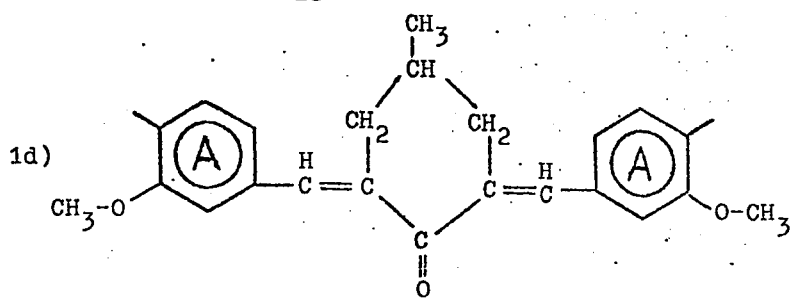

1e) 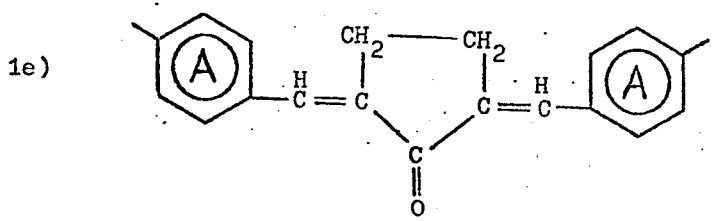

2. A polyglycidyl ether according to claim 1 wherein M denotes a chalcone radical of Formula (1a).

3. A polyglycidyl ether according to claim 1 wherein M denotes a chalcone radical of Formula (1b).

4. A polyglycidyl ether according to claim 1 wherein M denotes a chalcone radical of Formula (1c).

5. A polyglycidyl ether according to claim 1 wherein M denotes a chalcone radical of Formula (1d).

6. A polyglycidyl ether according to claim 1 wherein M denotes a chalcone radical of Formula (1e).

7. A composition which can be cured like a thermosetting resin and is characterized in that it contains an epoxy resin curing agent and at least one polyglycidyl ether of Formula I as defined in claim 1.

8. A composition according to claim 7 wherein the polyglycidyl ether component of Formula I is as defined in claim 2.

9. A composition according to claim 7 wherein the polyglycidyl ether component of Formula I is as defined in claim 3.

10. A composition according to claim 7 wherein the polyglycidyl ether component of Formula I is as defined in claim 4.

11. A composition according to claim 7 wherein the polyglycidyl ether component of Formula I is as defined in claim 5.

12. A composition according to claim 7 wherein the polyglycidyl ether component of Formula I is as defined in claim 6.

13. A composition according to claim 7 characterized in that it contains an organic acid anhydride or an organic amine epoxy resin curing agent.

14. A composition according to claim 13 wherein the curing agent is selected from the group consisting of maleic anhydride, methylnadic anhydride, and 4,4'-diaminodiphenylsulphone.

* * * * *

UNITED STATES PATENT OFFICE
CERTIFICATE OF CORRECTION

Patent No. 3,937,685  Dated February 10, 1976

Inventor(s) Herbert Kölbel, et al.

It is certified that error appears in the above-identified patent and that said Letters Patent are hereby corrected as shown below:

Col. 3, line 11 (page 6, line 1):
    "base"        should read -- case --.

Col 9, line 11 (page 16, line 5):
   Col. 3 Heading in Table II - "Valve E" should read -- Value E --.

Col. 9, bottom of page (Table III); (page 18, upper third of page):
   Each Example consists of four lines; "t" (duration of the principal curing reaction in hours) is measured in each Example, 1-4, at 20, 40, 100, and 200.

Signed and Sealed this

Sixth Day of July 1976

[SEAL]

Attest:

RUTH C. MASON
*Attesting Officer*

C. MARSHALL DANN
*Commissioner of Patents and Trademarks*